United States Patent
Chang et al.

(10) Patent No.: US 12,297,224 B2
(45) Date of Patent: May 13, 2025

(54) CRYSTAL FORM, PREPARATION METHOD, AND APPLICATION OF 4'-SUBSTITUTED NUCLEOSIDE

(71) Applicant: Henan Genuine Biotech Co., Ltd., Pingdingshan (CN)

(72) Inventors: Junbiao Chang, Zhengzhou (CN); Jinfa Du, Zhengzhou (CN); Kaikai Zhu, Zhengzhou (CN); Kai Wang, Zhengzhou (CN); Jianyong Li, Zhengzhou (CN); Chunxia Zhang, Zhengzhou (CN)

(73) Assignee: HENAN GENUINE BIOTECH CO., LTD., Pingdingshan (CN)

( * ) Notice: Subject to any disclaimer, the term of this patent is extended or adjusted under 35 U.S.C. 154(b) by 962 days.

(21) Appl. No.: 17/604,451

(22) PCT Filed: Mar. 21, 2019

(86) PCT No.: PCT/CN2019/078992
§ 371 (c)(1),
(2) Date: Oct. 18, 2021

(87) PCT Pub. No.: WO2020/007070
PCT Pub. Date: Jan. 9, 2020

(65) Prior Publication Data
US 2023/0151048 A1    May 18, 2023

(30) Foreign Application Priority Data

Jul. 2, 2018   (CN) .......................... 201810722856.8

(51) Int. Cl.
| | |
|---|---|
| C07H 19/16 | (2006.01) |
| A61K 31/505 | (2006.01) |
| A61K 31/5383 | (2006.01) |
| A61K 31/553 | (2006.01) |
| A61K 31/675 | (2006.01) |
| A61K 31/683 | (2006.01) |
| A61K 31/7068 | (2006.01) |
| A61K 31/7076 | (2006.01) |
| A61K 38/16 | (2006.01) |
| A61P 31/18 | (2006.01) |
| C07H 19/06 | (2006.01) |

(52) U.S. Cl.
CPC .......... *C07H 19/16* (2013.01); *A61K 31/505* (2013.01); *A61K 31/5383* (2013.01); *A61K 31/553* (2013.01); *A61K 31/675* (2013.01); *A61K 31/683* (2013.01); *A61K 31/7068* (2013.01); *A61K 31/7076* (2013.01); *A61K 38/162* (2013.01); *A61P 31/18* (2018.01); *C07H 19/06* (2013.01); *C07B 2200/13* (2013.01)

(58) Field of Classification Search
CPC ........ A61P 31/12; A61P 31/18; A61K 31/505; A61K 31/7076; C07B 2200/13
See application file for complete search history.

(56) References Cited

U.S. PATENT DOCUMENTS

| | | | |
|---|---|---|---|
| 8,039,614 B2 * | 10/2011 | Kohgo ................... | C07H 19/16 536/27.14 |
| 8,835,615 B2 * | 9/2014 | Chang .................... | C07H 19/14 536/22.1 |

FOREIGN PATENT DOCUMENTS

WO   WO2017139519 A1 *   8/2017   ......... A61K 31/7076

OTHER PUBLICATIONS

Hou (Journal of Medicinal Chemistry, 2023, 66, 11282-11293).*

* cited by examiner

*Primary Examiner* — Pancham Bakshi
(74) *Attorney, Agent, or Firm* — MATTHIAS SCHOLL P.C.; Matthias Scholl (57) ABSTRACT

The present invention discloses a crystal form, a preparation method and an application of a 4'-substituted nucleoside compound I having the following structure, including salts, prodrugs, and compositions thereof. Animal pharmacokinetic studies demonstrated that the effective drug concentrations of Compound Ia and Compound Ig in HIV target cells, peripheral blood mononuclear cells (PBMC), were effective in inhibiting HIV replication after 7 and 5 days, respectively. Therefore, Compound I can be used as a long-acting drug for preventing and treating AIDS. R is selected from ethynyl, azide, and cyano groups, X is selected from hydrogen and fluorine, and B is selected from B1 and B2.

2 Claims, 4 Drawing Sheets

CRYSTAL FORM, PREPARATION METHOD, AND APPLICATION OF 4'-SUBSTITUTED NUCLEOSIDE

CROSS-REFERENCE TO RELATED APPLICATIONS

This application is a National Stage Appl. filed under 35 USC 371 of International Patent Application No. PCT/CN2019/078992 with an international filing date of Mar. 21, 2019, designating the United States, now pending, and further claims foreign priority to Chinese Patent Application No. 201810722856.8 filed Jul. 2, 2018. Inquiries from the public to applicants or assignees concerning this document or the related applications should be directed to: Matthias Scholl P.C., Attn.: Dr. Matthias Scholl Esq., 245 First Street, 18th Floor, and Cambridge, MA 02142.

BACKGROUND

Field of the Invention

The disclosure relates to the field of medicinal chemistry, and more particularly, to 4'-substituted nucleoside derivatives and use thereof.

Description of the Related Art

The human immunodeficiency viruses (HIV) cause acquired immunodeficiency syndrome (AIDS) first clinically observed in 1981 in the United States. At present, 39 million people are estimated infected with HIV globally. AIDS is considered to be a threat to human health. HIV is replicated through adsorption, invasion, uncoating, reverse transcription, and integration of viral RNA into target genomic DNA, as well as synthesis, assembly, release, and maturation of viral protein. Each of the above procedures may include an inhibition target of a HIV drug. After more than 30 years of research, 40 AIDS drugs, including combination drugs, are approved by the Food and Drug Administration (FDA) for clinical use. The AIDS drugs are classified by the mechanism of action into nucleoside/nucleotide reverse transcriptase inhibitors, non-nucleotide reverse transcriptase inhibitors, protease inhibitors, entry inhibitors, integrase inhibitors, etc. The AIDS drugs inhibit the replication of HIV, but none of them can cure the disease. HIV develops resistance to the AIDS drugs after long-term treatment with the AIDS drugs and the AIDS drugs lose their potency. Treatment that uses a combination of different drugs is a standard treatment for the people newly diagnosed with HIV. HIV drug resistance still develops even if the HIV-infected patients undergo the combination therapy. Up to now the HIV-infected patients have to take drugs at least once a day during their long-term treatment. So continuing research to find a drug of a new mechanism for HIV control remains an important step to cure the disease.

2'-deoxynucleosides is a type of HIV inhibitor used in clinical practice and exerts its effect by blocking the reverse transcriptase. Currently the nucleotide reverse transcriptase inhibitors are all 3'-deoxynucleosides and lack a 3'-hydroxyl group on the deoxyribose moiety. As a result, following incorporation of the nucleotide reverse transcriptase inhibitors, the next incoming deoxynucleotide cannot form the next 5'-3' phosphodiester bond needed to extend the DNA chain. Thus, when a nucleotide reverse transcriptase inhibitor is incorporated, viral DNA synthesis and HIV replication are terminated. In recent years the nucleosides with a 3'-hydroxyl group, such as compound Id (CA Stoddart et al Antimicrob. Agents Chemother. 2015, 59, 4190) and compound Ig (Q. Wang et al Eur. J. Med. Chem. 2011, 46, 4178), have been reported to show potent activity against HIV. The nucleosides with a 3'-hydroxyl group all have a large substituent at the 4'-position, such as the ethynyl group in the compound Id and the azido group in the compound Ig. The nucleoside phosphates are incorporated into the viral DNA due to the introduction of the large substituent, and then the viral DNA synthesis and HIV replication are progressed slowly or terminated, because of steric hindrance.

For the adenosine, the introduction of 2-fluorine enhances the activity of 4'-ethynyl-2'-deoxyadenosine (EdA EC50=11 nM) against HIV by 2200 times (E. Michailidis et al J. Biol. Chem. 2009, 284, 35681). But the introduction of 2-fluorine into Tenofovir reduces the activity against HIV. It has been reported that the anti-HIV activity of tenofovir's phosphonic diamide is equal to that of phosphonic acid amide ester prodrugs (F. Pertusati, et al Eur. J. Med. Chem. 2014, 78, 259), with an EC50 of 0.019-0.03. In contrast, the anti-HIV activity of 2-fluoro-substituted tenofovir phosphonic acid diamide is reduced by 183-1377 times (EC50=5.51 uM), which illustrates that the 2-fluoro substitution causes unpredictable effects on the anti-HIV activity of drugs. The US patent (J. Chang U.S. Pat. No. 8,835,615, 2014) only discloses the chemical structure of compound Ia, and it is necessary to study its synthesis method and biological activity.

SUMMARY

Figure 1:
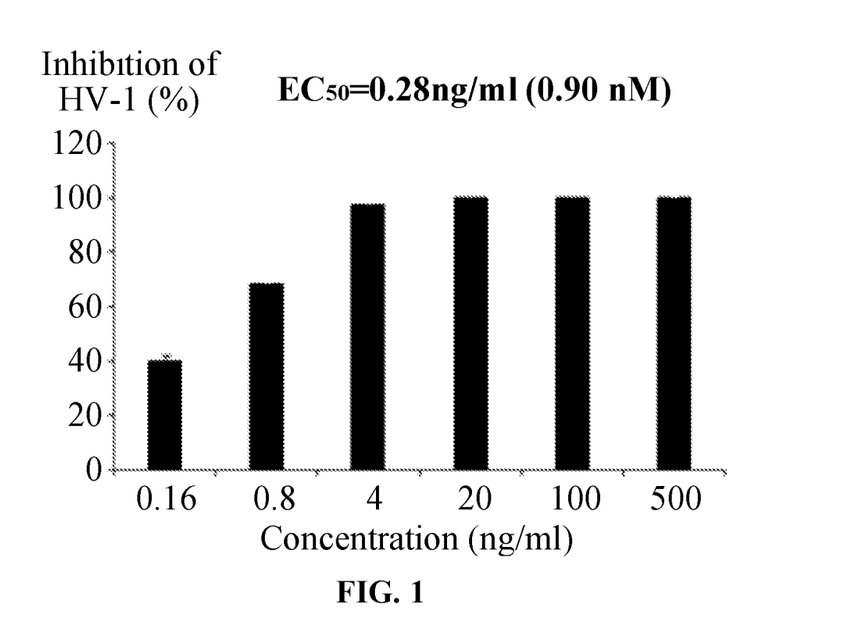
FIG. 1 is a histogram of anti-HIV activity of the compound Ia.
Figure 2:
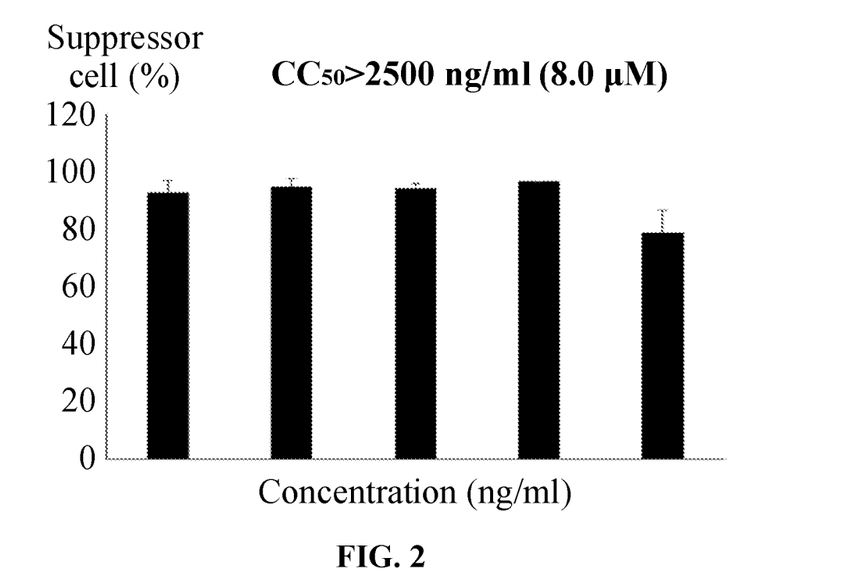
FIG. 2 is a histogram of the toxicity of the compound Ia to inhibit proliferation of HIV-infected cells.
Figure 3:
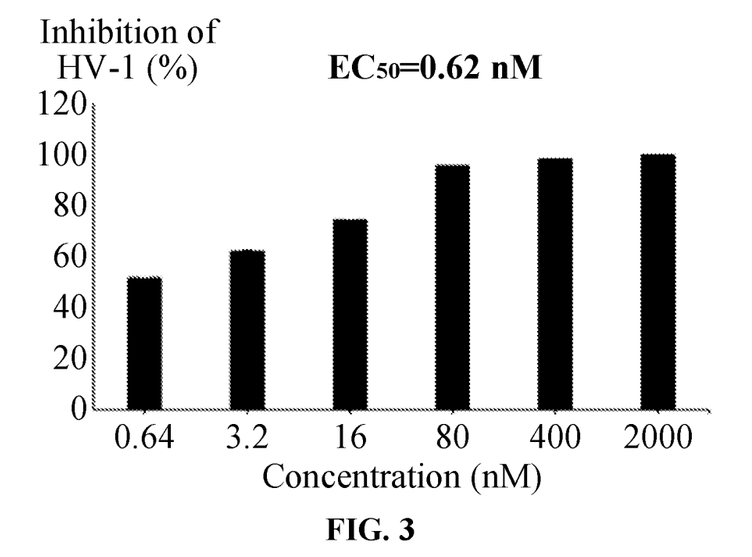
FIG. 3 is a histogram of anti-HIV activity of the compound Ib.
Figure 4:
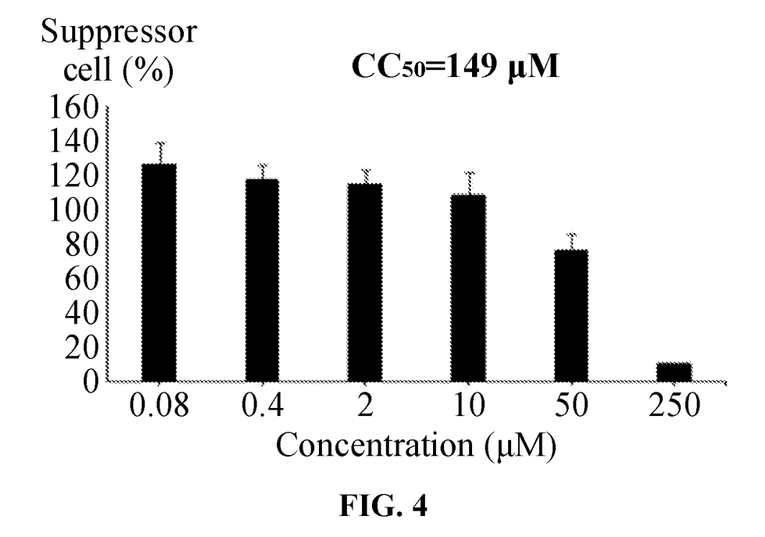
FIG. 4 is a histogram of the toxicity of the compound Ib to inhibit proliferation of HIV-infected cells.

The disclosure provides a compound Ia and a compound Ib for inhibiting replication of HIV, and the anti-HIV activity and cytotoxicity of the compounds Ia and Ib are measured. The disclosure suggests that the compounds Ia and Ib have potent anti-HIV activity (Ia: EC50=0.9 nM, as shown in FIG. 1; Ib: EC50=0.62 nM, as shown in FIG. 3) and show no obvious cytotoxicity (Ia: CC50>8000 nM, as shown in FIG. 2; Ib: CC50>149000 nM, as shown in FIG. 4) within the dosage range tested.

The compounds Ia and Ib are representative of a class of 4'-substituted nucleosides having formula I:

where R is ethynyl, azide or cyano;
X is hydrogen or fluorine;

B is B1 or B2.

In a class of this embodiment, the compounds of the formula I are Ia-Ig:

Ia

Ib

Ic

Id

Ie

If

Ig

The compounds Ia-Ig all contain a large substituent at the 4'-position, and show potent anti-HIV activity and metabolic stability.

Pharmacokinetics of the compound Ia after oral administration into rhesus monkeys. 6 mg/kg of compound Ia is orally administered to the Rhesus monkeys. The results show that the compound Ia is undetectable in plasma 24 hours after oral administration. In contrast, the active ingredient triphosphate (Ia-TP) of the compound Ia has a concentration of greater than 0.11 nM in HIV target cells and peripheral blood mononuclear cells (PBMC) of rhesus monkeys 168 hours (7 days) after oral administration. The half-life of effective drugs exceeds 72 hours in the target cells (Table 1). 20 mg/kg of clinic drug Lamivudine (3TC) is orally administered to the Rhesus monkeys. The results show that 3TC and other active ingredients are undetectable in the plasma and peripheral blood mononuclear cell (PBMC) of rhesus monkeys 24 hours after oral administration. Therefore, compared to the clinic drug 3TC, the compound Ia is better suitable to be a long-acting drug for prevention or treatment of HIV/AIDS. The long-acting property of the compound Ia may depend upon the introduction of 2-fluorine and a large substituent at the 4'-position. Compounds Ia-If are all 4'-substituted 2-fluoroadenine analogs capable of preventing or treating HIV/AIDS.

Figure 5:
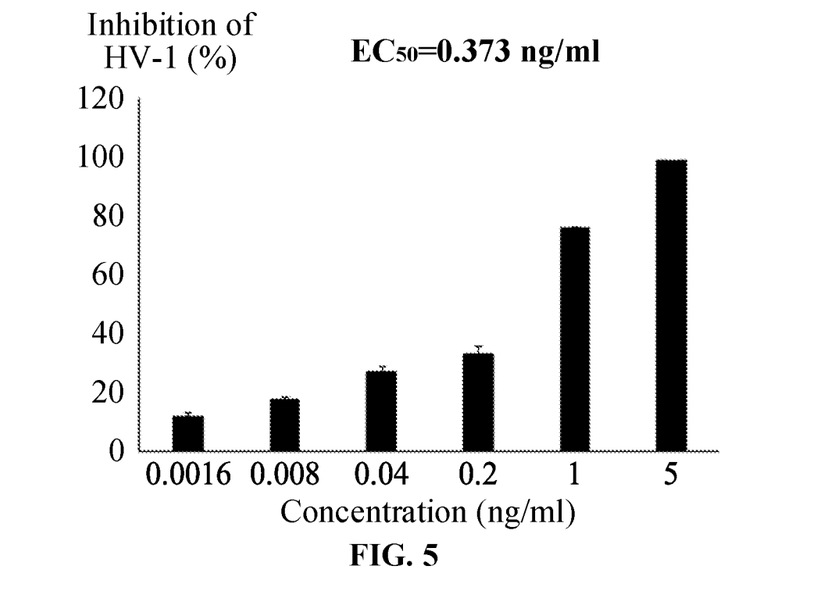
FIG. 5 is a histogram of anti-HIV activity of the compound Ig-TP.

The long-acting property of the compound that prevents or treats HIV/AIDS is measured. The anti-HIV activity of the triphosphate of the compound Ig (Ig-TP) is determined in CD4$^+$ T cells (Hut/CCR5). The results show that Ig-TP exhibits anti-HIV activity with a 50% effective concentration of 1.3 nM (EC50=0.073 ng/ml in FIG. 5) and with a 50% cell growth inhibition concentration of 8,134 nM (CC50=2,328 ng/ml).

Pharmacokinetics of compound Ig after oral administration into rhesus monkeys. 1 mg/kg (low-dose group) and 6 mg/kg (high-dose group) of the compound Ig are orally administered to the rhesus monkeys. The results show that the concentration of the compound Ig in the plasma increases with increasing dose. In the high-dose group, the concentration of compound Ig reaches 6.54 nM at 24 hours and fall below detection limit on the third day (Table 2); the concentration of compound Ig in HIV target cells and PBMC dropped to 0.09 pmol/$10^6$ cells 6 hours after oral administration and fall below detection limit after 24 hours; and after 120 hours (5 days), the concentration of the active ingredient (Ig-TP in Table 3) in PBMC remains at 1.35 nM, which is higher than the concentration (0.373 ng/mL, 1.3 nM) of the drugs required to inhibit 50% of HIV growth. The results show that the active ingredient can still inhibit HIV replication in HIV target cells 5 days after administration of the compound Ig to the rhesus monkeys. Therefore, the compound Ig is selected as a long-acting drug for prevention and treatment of HIV/AIDS.

The compound I, including Ia-Ig, as well as the salts, solvates, crystals, prodrugs, and a composition thereof, are used as active ingredients for preparation of a long-acting drug capable of preventing or treating HIV/AIDS. Those drugs are administered to the HIV-infected patients with an interval of 2 days or more.

The compound I may be used in combination with other HIV inhibitors to develop a new long-acting drug for prevention or treatment of HIV/AIDS. The other HIV inhibitors includes, but is not limited to, nucleoside inhibitors, non-nucleotide reverse transcriptase inhibitors, protease inhibitors, and integrase inhibitors. Optionally, the nucleoside inhibitors comprise zidovudine (AZT), didanosine (ddI), zalcitabine (ddC), stavudine (d4T), lamivudine (3TC), abacavir, emtricitabine (FTC), tenofovir (TDF), or islatravir (EFdA, MK-8591); the non-nucleotide reverse transcriptase inhibitors comprise nevirapine, delavirdine, efavirenz, or etraviren; the protease inhibitors comprise saquinavir, indinavir, ritonavir, nelfinavir, amprenavir, lopinavir, atazanavir, fosaprinavir, Ranavir, or Nonavir; and the integrase inhibitor includes: Letegravir, elitegravir, or dolutegravir.

The compound Ia may be used in combination with other HIV inhibitors to develop a new long-acting drug for prevention or treatment of HIV/AIDS. Preferably, the other HIV inhibitors comprise the compound Ig, tenofovir or tenofovir alafenamide, rilpivirine, dolutegravir, bictegravir, or albuvirtide.

The compound Ig may be used in combination with other HIV inhibitors to develop a new long-acting drug for prevention or treatment of HIV/AIDS. Preferably, the other HIV inhibitors comprise the compounds Ia-If, tenofovir or tenofovir alafenamide, rilpivirine, dolutegravir, bictegravir, and albuvirtide.

Unless otherwise stated, chemical terms used herein have the general meaning known to ordinary skill in the related art.

Unless otherwise stated, as used herein the term "protected" refer to a group is attached to an oxygen, nitrogen, or phosphorus atom so as to prevent the group from further reacting or achieving other purposes. Those skilled in the art will appreciate from the disclosure herein that there are a variety of protecting groups able to attach to oxygen and nitrogen atoms.

For any of the compounds disclosed herein, especially nucleosides or nucleotides, the hydroxyl or amino group may be protected or unprotected. It should be understood by those skilled in the art, "the hydroxyl or amino group is protected" means that the hydroxyl or amino group is protected by removable groups such as acyl, phosphono, phosphate, etc.

As used herein the term "pharmaceutically acceptable salt" comprise any salt of the compounds disclosed herein, such as sodium salt, potassium salt, ammonium salt, etc. The pharmaceutically acceptable salt refers to those non-toxic salts which retain the biological properties of the compounds disclosed herein and cannot cause unwanted side effects.

As used herein the term "Prodrug" refers to any compound that, when administered to a biological system, produces a biologically active compound due to a spontaneous chemical reaction, enzyme catalyzed reaction and/or metabolic process or a combination thereof. A standard prodrug may be connected to a functional group such as —OH, —NH$_2$, which is split in vivo to form a drug. Examples of prodrugs include esters, etc. The compounds that can form "ester" with the nucleoside compound I of the disclosure include various organic acids, for example, acetic acid and 3'-OH can form acetate, propionic acid and 3'-OH can form propionate. The prodrugs described are illustrative, but not restrictive, and those skilled in the art can synthesize other known prodrugs.

As used herein the term "solvates" refers to the nucleoside formula I or a salt thereof that combines a solvent in a chemically calculated amount or a non-chemically calculated amount through a non-covalent intermolecular force, and the solvent is water, so the solvates are hydrates.

As used herein the monophosphate group, diphosphate group and triphosphate group are shown as follows:

A method for preparing the compound Ia comprises:
(a) fluorinating a compound 1 with a fluorinating agent to form a compound 2;

$R^1$ is a protecting group for a hydroxyl group and includes, but is not limited to benzyl or substituted benzyl;

$R^2$ is a protecting group for a terminal alkyne and includes, but is not limited to the following group:

in (a), the fluorinating agent includes, but is not limited to, diethylaminosulfur trifluoride (DAST); or the hydroxyl group is activated by a leaving group and substituted by a fluoride ion to achieve fluorination; and the solvent for the fluorination reaction is an aprotic organic solvent;

(b) removing the protecting group from the compound 2 to form a compound Ia;

In (b), the reagent for removing the protecting group from the compound 2 includes, but is not limited to, metallic sodium-liquid ammonia, acids, and sulfonic acids, such as methanesulfonic acid.

The results of pharmacokinetic studies show that the compounds Ia and Ig can still inhibit HIV replication in HIV target cells and PBMC 7 days and 5 days after administration of effective concentration of the compounds Ia and Ig, respectively. Therefore, the compound I and the pharmaceutically acceptable salts thereof are selected as long-acting drugs for prevention or treatment of HIV/AIDS. The drugs are administered to the HIV-infected patients with an interval of 2 days or more.

DETAILED DESCRIPTION

To further illustrate, embodiments detailing 4'-substituted nucleoside derivatives and use thereof are described below. It should be noted that the following embodiments are intended to describe and not to limit the disclosure.

EXAMPLE 1

Preparation of compound 1

The compound 1 is prepared based on a method according to a literature (K. Fukuyama et al Org. Lett.2015,17, 828-831).

EXAMPLE 2

Preparation of compound Ia

Raw material 1 (9.64 g, 15.97 mmol, 1.0 eq) and pyridine (7.7 mL, 95.8 mmol, 6.0 eq) were added to 100 mL of dry toluene; diethylaminosulfur trifluorid (DAST) (15.4 g, 95.8 mmol, 6.0 eq) was dissolved in 40 mL of dry toluene; the resulting solution was added dropwise to the reaction solution at 0° C. in the presence of nitrogen; after the addition was complete, the reaction solution was heated to 50° C., refluxed for 6 hours, detected by liquid chromatography-mass spectrometry (LC-MS) until the reaction was completed, and cooled; the saturated sodium bicarbonate solution was added dropwise to the cooled reaction solution at the low temperature for quenching; the resulting solution was adjusted to pH 7-8, followed by addition of ethyl acetate (EA); the resulting organic phase was washed with water, washed with saturated sodium chloride solution, dried over anhydrous sodium sulfate, filtered, condensed, beated with polyethylene (PE), and filtered to yield 2.44 g of crude compound 2 which was directly used in the next step. 1H NMR (400 MHZ, CDCl3) δ 8.01 (d, J=2.0 Hz, 1H), 7.44-7.28 (m, 10H), 6.53 (dd, J=11.4, 5.1 Hz, 1H), 5.86 (s, 2H), 5.37 (dt, J=53.3, 4.9 Hz, 1H), 4.73 (s, 2H), 4.69-4.48 (m, 3H), 3.77 (dt, J=26.1, 6.2 Hz, 2H), 0.99 (t, J=7.9 Hz, 9H), 0.63 (q, J=8.0 Hz, 6H); $^{19}$F NMR (376 MHz, CDCl3) δ−50.83, −196.65.

The compound 2 (7.37 g crude product, 12.17 mmol, 1.0 eq) and ammonium fluoride (2.25 g, 60.83 mmol, 1.5 eq) were added to 50 mL of methanol, allowed to react at 50° C. for 6 hours in the presence of nitrogen, detected by liquid chromatography-mass spectrometry (LC-MS) until the reaction was completed; the resulting solvent was removed with a rotary evaporator, followed by addition of EA; the resulting organic phase was washed with water, washed with saturated sodium chloride solution, dried over anhydrous sodium sulfate, filtered, condensed, poured into a column using a dry packing method to yield 3.24 g of compound 3 (the total yield of the compounds 12 to 15 is about 30-40%). 1H NMR (400 MHz, CDCl$_3$) δ 7.94 (d, J=2.2 Hz, 1H), 7.42-7.27 (m, 10H), 6.54 (dd, J=12.1, 5.1 Hz, 1H), 6.03 (s, 2H), 5.56-5.21 (m, 1H), 4.82-4.49 (m, 5H), 3.76 (dt, J=26.5, 6.2 Hz, 2H), 2.73 (s, 1H).; $^{19}$F NMR (376 MHz, CDCl$_3$) δ−50.78, −195.84; m/z (ESI) (M+H)$^+$=492.2, m/z(ESI) (M+Na)$^+$=514.3.

The compound 3 (1.71 g, 3.48 mmol) was dissolved in 26 mL of chloroform, followed by dropwise addition of 6.84 mL of methanesulfonic acid; the mixture was allowed to react at room temperature for 5 hours in the presence of nitrogen, detected by liquid chromatography-mass spectrometry (LC-MS) until the reaction was completed; the saturated sodium bicarbonate solution was added dropwise to the resulting solution at a low temperature for quenching, adjusted to pH 7-8, followed by addition of EA. The organic phase is separated from the resulting solution, washed with saturated sodium chloride solution, dried over anhydrous sodium sulfate, filtered, condensed, and poured into a column (DCM:MeOH=20:1-10:1) using a dry packing method to yield a compound Ia (748 mg, 69%). 1H NMR (400 MHZ, MeOD) δ 8.25 (d, J=1.7 Hz, 1H), 6.46 (dd, J=8.9, 5.7 Hz, 1H), 5.35 (dt, J=53.9, 5.8 Hz, 1H), 4.75 (dd, J=22.3, 5.9 Hz, 1H), 3.88 (dd, J=12.3, 1.8 Hz, 1H), 3.80 (d, J=12.3 Hz, 1H), 3.22 (s, 1H).; 19F NMR (376 MHZ, MeOD) δ−53.22, −201.69; m/z (ESI) (M+H)$^+$=312.2, m/z (ESI) (M+Na)+=334.1.

Figure 7:
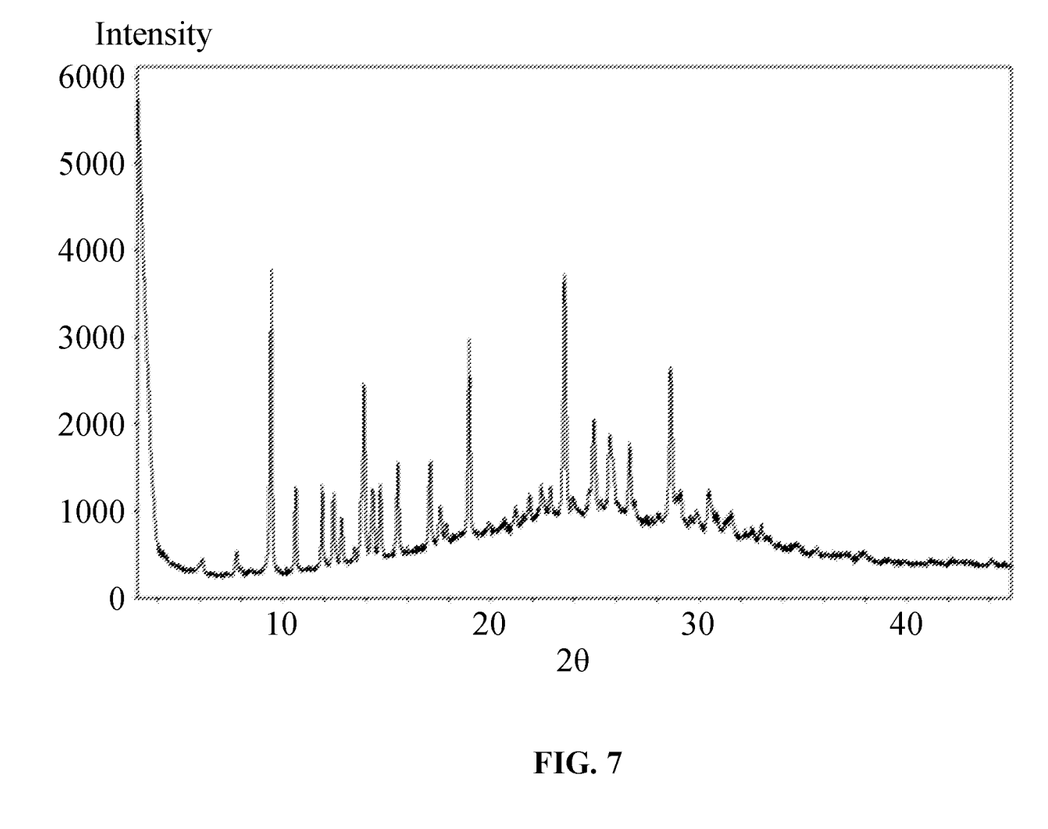
FIG. 7 is an XRPD spectrum of the compound Ia.

Referring to FIG. 7, the crystal A of the compound Ia had diffraction peaks at 2θ angles (+0.2): 6.13, 7.77, 9.43, 10.61, 11.88, 12.44, 12.80, 13.88, 14.28, 14.66, 15.51, 17.09, 17.55, 17.88, 18.95, 21.18, 21.86, 22.40, 22.87, 23.52, 24.93, 25.69, 26.63, 28.60, 30.46 in a diffraction spectrum using CuKα radiation with a wavelength of λ=1.5418 Å.

Diffraction peaks at 2θ angles and corresponding relative intensities (%) of the crystal A of compound Ia:

| 2θ (±0.2°) | Relative intensities I% |
| --- | --- |
| 6.13 | 4.5 |
| 7.77 | 7.7 |
| 9.43 | 100.0 |
| 10.61 | 28.0 |
| 11.88 | 26.7 |
| 12.44 | 23.7 |
| 12.80 | 14.6 |
| 13.88 | 58.2 |
| 14.28 | 22.8 |
| 14.66 | 23.2 |
| 15.51 | 30.5 |
| 17.09 | 27.6 |
| 17.55 | 12.6 |
| 17.88 | 5.9 |
| 18.95 | 65.2 |
| 21.18 | 6.4 |
| 21.86 | 7.4 |
| 22.40 | 11.2 |
| 22.87 | 9.7 |
| 23.52 | 79.3 |
| 24.93 | 29.6 |
| 25.69 | 24.5 |
| 26.63 | 23.5 |
| 28.60 | 52.1 |
| 30.46 | 13.4 |

EXAMPLE 3

Measurement of anti-HIV activity of the compounds Ia and Ib.
Materials and Methods
3.1 Compound
The compound Ia or compound Ib was dissolved in DMSO to achieve a final concentration of 10 mg/ml and stored at −20° C.
3.2 HIV-1
The plasmids used for packaging pseudotyped single-cycle infectious HIV-1 (HIV-luc/JRFL) are as follows: the plasma pLAI-Aenv-Luc contains HIV-1 isolate in which Env and Vpr genes are deleted and luciferase gene is inserted into the Nef locus; and the plasma pJRFL contains CCR5-tropic HIV-1 env gene; the two plasmas are co-transfected into HEK293T cells; the supernatant was collected, filtered, and packaged; and the virion capture was quantified by p248$^a$g ELISA.
3.3 Detection of HIV-1 infection
CD4$^+$ T cells (Hut/CCR5) were cultured in RPMI 1640 medium (Gibco) containing 10% fetal bovine serum (Gibco), 100 U/mL penicillin (Invitrogen), and 100 U/mL streptomycin (Invitrogen). 1×10$^5$ Hut/CCR5 cells were added to the compound Ia or Ib, infected with HIV-luc/JRFL (1 ng p24gag), incubated at 37° C. for 3 hours, washed to remove free virus, and resuspended in cell culture medium, followed by addition of the corresponding compound to be tested, incubated at 37° C. for 3 days, and collected for measurement of the luciferase activity and calculation of the percentage of viral inhibition. AZT was used as a control group (as shown in FIGS. 1 and 3).
3.4 Measurement of Cell Cytotoxicity (MTT Assay)
CD4$^+$ T cells (Hut/CCR5) were plated into the wells of a 96-well plate (1×10$^4$ uL/well), followed by addition of different compounds to be tested; the 96-well plate was incubated at 37° C. in an incubator for 3 days; 20 μL of MTT solution was added into the wells (5 mg/well) of the 96-well plate; the 96-well plate was incubated at 37° C. in the incubator for 4 hours; 100 μL of Formazan solution was added into the wells of the 96-well plate; the 96-well plate was incubated at 37° C. in the incubator until the complete dissolution of Formazan was observed by a common optical microscope; and the absorbance of the solution was measured at 570 nm (as shown in FIGS. 2 and 4).

EXAMPLE 4

Figure 6:
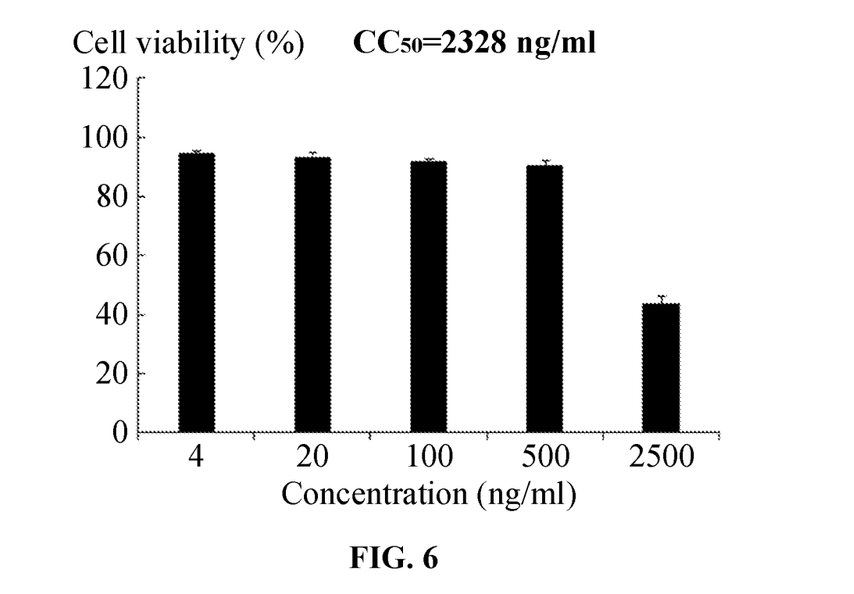
FIG. 6 is a histogram of the toxicity of the compound Ig-TP to inhibit proliferation of HIV-infected cells.

Measurement of Anti-HIV Activity of the Compound Ig-TP
Materials and Methods
4.1 Measurement of the Anti-HIV Activity and Cell Cytotoxicity of the Compound Ig-TP (CL-002-TP).
4.2 Measurement Method CD4+ T cells (Hut/CCR5) were cultured in 1640 medium (Gibco) containing 10% fetal bovine serum (Gibco), 100 U/mL penicillin (Invitrogen), and 100 U/mL streptomycin (Invitrogen). $1 \times 10^5$ Hut/CCR5 cells were added to the compound Ig-TP (CL-002-TP), infected with HIV-luc/JRFL (1 ng p24gag), incubated at 37° C. for 3 hours, washed to remove free virus, and resuspended in cell culture medium, followed by addition of the corresponding compound to be tested, incubated at 37° C. for 3 days, and collected for measurement of the luciferase activity and calculation of the percentage of virus inhibition. AZT was used as a control group (as shown in FIGS. 1 and 3).
4.3 Experimental Results The cytotoxicity of the compound Ig-TP on CD4+ T cells (Hut/CCR5) was measured using MTT assay. The results show that the compound Ig-TP has a low toxicity to CD4+ T cells, with a cytotoxic concentration (CC50) value of 2,328 ng/ml (8,134 nM in FIG. 5). The results also show that the compound Ig-Tp is potent in inhibiting HIV viral proliferation (as shown in FIG. 6, IC50=0.373 ng/ml, 1.3 nM).

EXAMPLE 5

Active metabolites of compounds Ia, 3TC, and Ig in PBMC of rhesus monkey
5.1 Experimental Materials
5.2 Drugs and Reagents
  Compounds Ia, 3TC, and Ig (CL-002);
  Ia-TP, 3TC-TP, Ig-TP;
  Anticoagulant EDTAK2, which is purchased from Shanghai Institute of Chemical Reagents;
  Normal saline, which is purchased from Shanghai Chemical Reagent Station Sub-assembly Factory; and
  Lymphocyte separation medium (Ficoll-Paque PLUS, 1.077 g/mL, 6×100 mL), GE Healthcare.
5.3 Experimental Equipment
  3 mL pasteur pipette;
  50 ml horizontal centrifuge, no braking;
  Electronic analytical balance, OHAUS, USA;
  KQ5200 Ultrasonic Cleaner, Kunshan Ultrasonic Instrument Co., Ltd.; and
  10 μL, 200 uL, and 1 mL pipettes, Eppendorf, Germany.
5.4 Laboratory Animals
  Two male rhesus macaques weighing 8 and 9 kg, were provided by Henan Normal University.
5.5 Preparation of Blank Plasma from Rhesus Monkeys.

The two male rhesus macaques were fasted without access to water for 12 hours; 15-20 mL of venous blood was collected from the hind limbs of each male rhesus macaque; 3 mL of venous blood was centrifuged at 3000 rpm for 10 minutes to separate the plasma from the venous blood, and stored below −20° C. The PBMC was separated from the remaining venous blood with Ficoll-Paque separation medium, condensed to 0.3 mL of cell suspension, counted, and stored below −20° C.
5.6 Pharmacokinetics of the compounds Ia, Ig (CL-002) and 3TC after oral administration into rhesus monkeys: 130 mg of the compound CL-002 was added to 21.7 mL of normal saline, and sonicated at 40° C. for 15 minutes to yield a liquid medicine with a concentration of 6 mg/mL; the liquid medicine was diluted to 1 mg/mL in a ratio of 1:5; 6 mg/mL of the liquid medicine is used as a high-dose group and 1 mg/mL of the liquid medicine is used as a low-dose group; the dosage volume was 1 mL/kg; and the compound CL-002 was administered to the rhesus monkeys at 6 mg/kg and 1 mg/kg, respectively (the compound 3TC was administered to the rhesus monkeys at 20 mg/kg; and the compound Ia was to the rhesus monkeys at 6 mg/kg).

The two male rhesus macaques were randomly divided into a high-dose group and a low-dose group, and one rhesus macaque in each group; the two healthy rhesus macaques are fasted without access to water 12 hours; 1 mg/kg and 6 mg/kg of the compound CL-002 (or 20 mg/kg of 3TC) were orally administered to the rhesus macaques; 15-20 ml of venous blood was collected from the hind limbs of rhesus macaque at 1 h, 6 h, 24 h, 3 days, 5 days, and 7 days after administration; 1 mL of venous blood was centrifuged at 3000 rpm for 10 min to separate the plasma from the venous blood; and stored below −20° C. The PBMC was separated from the remaining venous blood with Ficoll-Paque separation medium, condensed to 0.3 mL of cell suspension, counted, and stored frozen below −20° C.

5.7 Measurement of the compounds Ia, 3TC and Ig: 50 μL of the plasma was aspirated; 50 μL of internal standard solution (3TC, 50 ng/ml) and 200 μL of methanol were added to the 50 μL of the plasma in order, vortexed on a vortex mixer for 30 seconds, and centrifuged at 13000 rpm for 5 minutes; 250 μL of the supernatant was transferred to a 10 mL round-bottom glass tube, dried in a stream of nitrogen at 50° C., redissolved in 250 mL of methanol solution (methanol: water=1:1), vortexed for 60 minutes, transferred into a 1.5 mL EP tube, centrifuged at 13000 rpm for 5 minutes, filtered, and centrifuged to obtain 10 μL of supernatant for LM-MS/MS analysis.
5.8 Measurement of the Compounds Ia, 3TC and Ig in PBMC.

The PBMC sample was crushed with an ultrasonic cell crusher, followed by addition of 3 times volume of acetonitrile, vortexed for 60 seconds, followed by 1 volume of the water, vortexed for 60 seconds, and centrifuged at 3000 rpm for 5 minutes; the supernatant was aspirated, transferred into a 10 mL round-bottom glass tube, dried in a stream of nitrogen at 40° C., and redissolved in 500 μL of methanol solution (methanol: water=2:8 (v/v)); the resulting solution was vortexed for 60 seconds, transferred into a 1.5 mL EP tube, centrifuged at 13000 rpm for 5 minutes, filtered, and centrifuged to obtain 10 L of supernatant for LM-MS/MS analysis.
5.9 Experimental Results

TABLE 1

Drug concentration in PBMC after oral administration of compound Ia or 3TC in rhesus monkeys

| Drug Concentration dosage | Compound Ia-TP (pmol/$10^6$ cells) 6 mg/kg | Compound 3TC-TP (pmol/$10^6$ cells) 20 mg/kg |
|---|---|---|
| 1 h | 0.34 | 0.51 |
| 6 h | 0.51 | 2.45 |
| 24 h | 0.92 | ND |
| 72 h | 0.57 | ND |
| 120 h | 0.11 | ND |
| 168 h | >0.10 | ND |

ND: Not Detected.

TABLE 2

Drug concentration in plasma after oral administration of compound Ig (CL-002) in rhesus monkeys

| Drug Concentration | Compound Ig (Pmol/10$^6$ cells) | |
| --- | --- | --- |
| dosage | 1 mg/kg | 6 mg/kg |
| 1 h | 196.50 | 2068.29 |
| 6 h | 3.15 | 204.48 |
| 24 h | ND | 6.54 |
| 72 h | ND | ND |
| 120 h | ND | ND |
| 168 h | ND | ND |

ND: Not Detected.

TABLE 3

Drug concentration in PBMC after oral administration of compound Ig (CL-002) in rhesus monkeys

| Drug Concentration | Compound Ig (pmol/10$^6$ cells) | | Compound Ig-TP (pmol/10$^6$ cells) | |
| --- | --- | --- | --- | --- |
| dosage | 1 mg/kg | 6 mg/kg | 1 mg/kg | 6 mg/kg |
| 1 h | 0.025 | 0.44 | 0.39 | 0.23 |
| 6 h | ND | 0.09 | 2.10 | 4.07 |
| 24 h | ND | ND | 0.29 | 0.44 |
| 72 h | ND | ND | 0.66 | 1.85 |
| 120 h | ND | ND | 0.54 | 1.35 |
| 168 h | ND | ND | ND | ND |

ND: Not Detected.

What is claimed is:

1. A crystal form A of a compound of formula Ia:

wherein a CuKα X-ray powder diffraction (XRPD) spectrum of the crystal form A has diffraction peaks at diffraction angle 2θ positions of 6.13°±0.2°, 7.77°±0.2°, 9.43°±0.2°, 10.61°±0.2°, 11.88°±0.2°, 12.44°±0.2°, 12.80°±0.2°, 13.88°±0.2°, 14.28°±0.2°, 14.66°±0.2°, 15.51°±0.2°, 17.09°±0.2°, 17.55°±0.2°, 17.88°±0.2°, 18.95°±0.2°, 21.18°±0.2°, 21.86°±0.2°, 22.40°±0.2°, 22.87°±0.2°, 23.52°±0.2°, 24.93°±0.2°, 25.69°±0.2°, 26.63°±0.2°, 28.60°±0.2° and 30.46°±0.2°.

2. A method for prevention or treatment of AIDS, the method comprising administering to a patient in need thereof a pharmaceutical composition comprising the crystal form A of the compound of formula Ia of claim 1.

* * * * *